United States Patent [19]
Cimbollek et al.

[11] Patent Number: 5,679,646
[45] Date of Patent: Oct. 21, 1997

[54] SOLVENT FOR A SPARINGLY SOLUBLE GENTAMICIN SALT

[75] Inventors: Monika Cimbollek, Mannheim; Berthold Nies, Ober-Ramstadt, both of Germany

[73] Assignee: Merck Patent Gesellschaft mit Beschrankter Haftung, Germany

[21] Appl. No.: 238,086

[22] Filed: May 4, 1994

[30] Foreign Application Priority Data

May 5, 1993 [DE] Germany ............. 43 14 871.9

[51] Int. Cl.$^6$ ............................ A61K 31/70
[52] U.S. Cl. ............................ 514/43; 536/13.6
[58] Field of Search ................ 536/13.6; 514/43, 514/25

[56] References Cited

U.S. PATENT DOCUMENTS

| | | | |
|---|---|---|---|
| 4,212,860 | 7/1980 | Mc Combie | 429/180 |
| 4,843,112 | 6/1989 | Gerhart et al. | 523/114 |
| 4,937,257 | 6/1990 | Gericke et al. | 514/456 |

OTHER PUBLICATIONS

The Merck Index, ninth edition (1976), p. 1187 No. 8929.

H. Wahlig et al., "Pharkokinetik und Gewebeverträglichkeit einer Tricalciumphosphate . . . ", Z Zahnärztl Implantol III, pp. 179–182 (1987).

*Primary Examiner*—Elli Peselev
*Attorney, Agent, or Firm*—Millen, White, Zelano & Branigan, P.C.

[57] ABSTRACT

A solvent for the salt of gentamicin with 3-p-methoxybenzylidene-6-hydroxy-4'-methoxyflavanone-6-phosphate which is a mixture of from 6 to 9.75 parts by volume of tetrahydrofuran and from 4 to 0.25 parts by volume of water. In these solvents the active compound is soluble up to about 60% by weight. Such a solution is particularly suitable for loading pharmaceutical carriers with this active compound.

11 Claims, No Drawings

SOLVENT FOR A SPARINGLY SOLUBLE GENTAMICIN SALT

The invention relates to a solvent for a sparingly soluble salt of the pharmaceutical active compound gentamicin and also a process for loading pharmaceutical active compound carriers with this salt.

BACKGROUND OF THE INVENTION

Gentamicin belongs to the aminoglycoside class of antibiotics and has a pronounced broad-spectrum action. Owing to its specific spectrum of action, gentamicin has, in particular, also proven useful in the local treatment of bone infections. Gentamicin is generally used in its sulfate form. However, the sulfate salt is readily soluble in water and physiological media. Local treatment with gentamicin sulfate, for example by implantation of active compound carriers loaded with gentamicin sulfate at the site of the infection or treatment, is generally characterized by an initial short-term build-up to a high active compound concentration which then drops very quickly. This can be shown, for instance, by in vitro elution experiments or by measurement of the serum concentration in-vivo. However, it is therapeutically desirable to have a long-lasting active compound concentration which, depending on the amount charged, preferably remains constant for weeks or months and decreases only slowly. Owing to the good water-solubility of gentamicin sulfate, it has not been possible to achieve protracted release through appropriate pharmaceutical formulations of this active compound and the active compound carriers.

DE 34 31 534, which corresponds to U.S. Pat. No. 4,937,257, discloses a salt of gentamicin with 3-p-methoxybenzylidene-6-hydroxy-4'-methoxyflavanone-6-phosphate, hereinafter designated as "gentamicin salt". This salt is sparingly soluble in water and aqueous media. However, it has been found that in an aqueous medium this salt slowly eliminates and releases gentamicin. Therefore, this gentamicin salt is usable as a depot antibiotic providing a reservoir or depot of the active ingredient for controlled release and is especially suitable for use as an antibiotic active compound in pharmaceutical carriers with protracted release. Corresponding findings are, for example, described in Z. Zahnärztl. Implantol. III, 179 to 182 (1987).

However, the sparing solubility of this gentamicin salt is accompanied by considerable disadvantages in the loading of active compound carriers. With a maximum solubility of the gentamicin salt in water of about 0.5% by weight, porous active compound carriers such as calcium phosphate ceramics or structured collagen can normally be loaded with only a limited amount of active compound by impregnation with the corresponding solution and drying. Repetition of the impregnation and drying procedure is, if practical at all, complicated and also leads to non-uniform active compound distribution in the carrier material and thus to considerable scatter in the rates of release. The same applies to the corresponding use of aqueous suspensions of this active compound.

SUMMARY OF THE INVENTION

It is therefore an object of this invention to find a solvent or solvent system in which the described gentamicin salt is readily soluble and which can be used to prepare gentamicin salt solutions with a content of more than 10% by weight of the salt which are preferably suitable for the loading of pharmaceutical carriers with this active compound.

Upon further study of the specification and appended claims, further objects and advantages of this invention will become apparent to those skilled in the art.

Systematic investigations have now shown that the gentamicin salt is sparingly soluble not only in water but also in practically all customary organic solvents.

Table 1 shows the maximum solubilities of the gentamicin salt in various solvents and Table 2 shows those in various solvent mixtures.

TABLE 1

Maximum solubilities of the gentamicin salt in various solvents

| Solvent | max. solubility in mg/ml (20° C.) |
| --- | --- |
| Water | 0.6 |
| Water pH 9 (NH$_4$OH) | ≦100 |
| Methanol | 9 |
| Ethanol | 0.1 |
| Isopronanol | <1 |
| Acetone | <1 |
| Chloroform | 5 |
| Dichloromethane | <10 |
| 1,1,1-Trichloroethane | <5 |
| Diisopropyl ether | <5 |
| Methyl t-butyl ether | <5 |
| THF | 50 |
| Methyl ethyl ketone | <5 |
| Cyclohexane | <5 |
| DMF | <5 |

TABLE 2

Maximum solubilities of the gentamicin salt in various solvent mixtures

| Solvent mixture | (volume ratio) | max. solubility in mg/ml (20° C.) |
| --- | --- | --- |
| Methanol/dichloromethane | 7:3 | 10 |
| Methanol/ethyl acetate | 1:1 | <1 |
| Acetone/methanol | 7:3 | <1 |
| Isopropanol/methanol | 7:3 | <1 |
| THF/methanol | 4:1 | 30 (50° C.) |
| DMF/methanol | 1:1 | 50 (50° C.) |
| Additions of 10–50% by volume of water to methanol, ethanol and acetone | | <1 |

These tables show that only solutions having a content of the gentamicin salt significantly below 1% by weight can be prepared with most of the solvents or mixtures. In a few cases, contents between 1 and about 5% by weight can be achieved. The highest possible concentration of about 10% by weight can only be obtained in water having an increased pH. However, in aqueous alkaline solution the active compound is unstable and decomposes, even when in carrier materials treated therewith. This possibility is thus unsuitable for the proposed purpose. A fundamental improvement in the solubility properties by addition of surfactants or other substances known as solubilizers, such as higher alcohols, is likewise out of the question.

However, it has now been found, completely surprisingly, that mixtures of from 6 to 9.75 parts by volume of tetrahydrofuran and from 4 to 0.25 parts by volume of water are excellent solvents for the otherwise sparingly soluble gentamicin salt. In these mixtures, the salt can be easily dissolved in concentrations up to about 60% by weight, particularly from 14 to 60% by weight.

The invention accordingly provides a solvent for the gentamicin salt, which solvent comprises a mixture of from 6 to 9.75 parts by volume of tetrahydrofuran and from 4 to 0.25 parts by volume of water, preferably 7 to 9 parts by volume of tetrahydrofuran and 3 to 1 parts by volume of water, and particularly preferably, about 9 parts by volume of tetrahydrofuran to 1 part by volume of water.

The invention also provides for the use of such a mixture as a solvent for the gentamicin salt and also a process for preparing gentamicin salt solutions in which the salt is dissolved in such a mixture.

The invention further provides solutions of the gentamicin salt in such mixtures and also a process for treating pharmaceutical active compound carriers with this salt, in which the carrier is treated with such a solution.

Table 3 shows the maximum solubilities of the gentamicin salt in tetrahydrofuran/water mixtures of various volume compositions.

TABLE 3

Maximum solubilities of the gentamicin salt in tetrahydrofuran/water mixtures of various volume compositions

| THF/H$_2$O mixture (volume ratio) | max. solubility in mg/ml (20° C.) |
| --- | --- |
| 10.00:0.00 | 50 |
| 9.75:0.25 | 140 |
| 9.5:0.5 | 250 |
| 9.0:1.0 | 600 |
| 8.0:2.0 | 550 |
| 7.0:3.0 | 500 |
| 6.0:4.0 | 140 |
| 5.0:5.0 | <100 |

THF/water mixtures in the composition range of 6 to 9.75:4 to 0.25 show a dramatic solubility increase to active compound contents of from 14 to 60% by weight in the solution. The solubility is at a maximum in the range of tetrahydrofuran to water between 7:3 and 9:1. Outside the range of 6–9.75:4–0.25, the solubilities lie below 10% by weight. This finding is surprising and, because of the obviously otherwise general sparing solubility of the salt (see Tables 1 and 2), could not be foreseen.

Preparation of the gentamicin salt solution involves simply introducing the active compound into the solvent mixture of the invention and dissolving while stirring. The desired concentration within the solubility range is set by appropriate matching of the amounts of gentamicin salt and solvent mixture. The preferred composition of the mixture is 9 parts by volume of tetrahydrofuran to 1 part by volume of water. It has been found that the dissolution proceeds most quickly at this ratio. Gentle warming up from, e.g., room temperature, to about 50° C. can accelerate the dissolution. A subsequent fine filtration may also be advantageous.

The gentamicin salt solutions of the invention are particularly suitable for loading pharmaceutical carriers with the active compound. Unlike the methods hitherto possible, by which gentamicin salt solutions having a content of at most 10% by weight were preparable, the solvent mixture of the invention makes available highly concentrated solutions with contents of up to about 60% by weight. These solutions easily make possible carrier-bound depot forms of gentamicin having high dosage and thus high local concentration of active compound. By "depot form" it is meant, for example, that a reservoir or depot of the active ingredient is provided for controlled release.

Suitable carrier materials are firstly porous materials which readily absorb the active compound solution. Preference is given to bioactive and in particular bioabsorbable materials which are preferably present in the form of shaped implants used, for example, in the body of a patient internally. These shaped implants principally aid bone replacement in the treatment or reconstitution of bone defects caused by accidents or illness. The shaped bodies can, however, also be used as depot implants for the local release of an active compound in fighting or preventing infections.

Typical porous biomaterials for such shaped implants are calcium phosphates such as, in particular, calcium phosphate ceramics. In general these include hydroxyapatite of synthetic or natural origin. Further calcium phosphate materials are tricalcium phosphate and tetracalcium phosphate which are used analogously. Preference is also given to bone ceramics which can be obtained from natural bone by removal of the organic part of the bone and sintering the mineral part of the bone to a ceramic material. Spongiosa ceramic is also particularly suitable for impregnation with the active compound because of the naturally high porosity. Porous shaped implants of bioinert polymer materials such as, for example, polytetrafluoroethylene ("Teflon") or of biopolymers such as collagen, gelatin, polylactides or polyglycolides can likewise be treated with the gentamicin salt solution of the invention. These materials are preferably used in the form of absorbent bodies having a sponge-like, nonwoven or woven structure. Porous composite materials of bioceramics and biopolymers are likewise suitable for use as active compound carriers.

The loading of the porous active compound carriers with the gentamicin salt solution of the invention is carried out by treating the carrier with the active compound solution by complete immersion or by dripping the solution onto the carrier until the absorption capacity of the carrier is completely met by the solution. The carrier is then dried, preferably in a stream of warm air. Drying occurs relatively quickly since the tetrahydrofuran, which is the main component of the solvent mixture, evaporates rapidly. By this method, the inner and outer surfaces of the shaped bodies acquire a very substantially uniform coating of the active compound. After any required sterilization and sterile packaging, the shaped implants loaded with the active compound are ready for use.

By analogous treatment with the gentamicin salt solution of the invention, even nonporous implants or implants which only have a rough surface can be coated with a layer of active compound. Such an antibiotic coating provides protracted release of active compound and is thus advantageous for application to many types of endoprostheses made of metal, ceramic or plastic. For this use, besides the high active compound concentration, the solution of the invention has the further advantage that it readily wets and uniformly coats materials which are otherwise not wetted by purely aqueous solutions. For example, it can be advantageously used for the antibiotic coating of the femur shaft of a hip endoprostheses.

The entire disclosure of all applications, patents and publications, including priority document German Patent No. P 43 14 871.9, filed May 5, 1993 in Germany, cited above and below are hereby incorporated by reference.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

EXAMPLES

Example 1: Preparation of the Gentamicin Salt Solution 1.5 g of the salt of gentamicin with 3-p-methoxybenzylidene-6-hydroxy-4'-methoxyflavanone-6-phosphate are added to a mixture of 9 ml of tetrahydrofuran and 1 ml of water and dissolved at 25° C. with stirring.

Example 2: Treatment of Carriers of Spongiosa Ceramic

Blocks of porous hydroxyapatite ceramics made from natural spongiosa and having dimensions of 12.5×12.5×10 mm are impregnated with the solution of Example 1 by immersion. The ceramic blocks fully soaked with solution are taken out and dried for about 2 hours in a stream of warm air. The ready-to-use blocks contain 30 mg of the gentamicin salt.

Example 3: Loading of a Nonwoven Teflon

A circular nonwoven Teflon having a diameter of 0.5 cm and a thickness of 1.45 mm is immersed in the solution of Example 1 until it is completely soaked. It is then taken out and dried for about 30 minutes in a stream of warm air. The ready-to-use nonwoven Teflon contains 63 mg of gentamicin salt.

We claim:

1. A process for preparing a solution of the salt of gentamicin with 3-p-methoxybenzylidene-6-hydroxy-4'-methoxyflavanone-6-phosphate, which comprises dissolving the salt in a mixture of from 6 to 9.75 parts by volume of tetrahydrofuran and from 4 to 0.25 parts by volume of water, such that the prepared solution has a content of at least 10% by weight of the salt in solution.

2. The process of claim 1, wherein the salt is dissolved in a mixture of from 7 to 9 parts by volume of tetrahydrofuran and 3 to 1 parts by volume of water.

3. The process of claim 2, wherein the prepared solution has a content of about 50 to 60% by weight of the salt in solution.

4. A solution of the salt of gentamicin with 3-p-methoxybenzylidene-6-hydroxy-4'-methoxyflavanone-6-phosphate with a solvent which is a mixture of from 6 to 9.75 parts by volume of tetrahydrofuran and from 4 to 0.25 parts by volume of water, wherein the solution has a content of at least 10% by weight of the salt in solution.

5. The solution of claim 4, wherein the solvent is a mixture of 7 to 9 parts by volume of tetrahydrofuran and 3 to 1 parts by volume of water.

6. The solution of claim 5, having a content of about 50 to 60% by weight of the salt in solution.

7. A process for loading a carrier suitable for carrying a pharmaceutically active compound with the salt of gentamicin with p-methoxybenzylidene-6-hydroxy-4'-methoxyflavanone-6-phosphate, comprising treating the carrier with the solution of claim 6, and then removing the solve by drying.

8. The process of claim 7, wherein the solvent in the solution is a mixture of 7 to 9 parts by volume of tetrahydrofuran and 3 to 1 parts by volume of water.

9. The process of claim 8, wherein the solution has a content of about 50 to 60% by weight of the salt in solution.

10. The process of claim 7, wherein the carrier is a biocompatible material in the form of a shaped implant.

11. The process of claim 10, wherein the biocompatible material in the form of a shaped implant is a calcium phosphate material.

* * * * *